United States Patent [19]

Nakauchi

[11] Patent Number: 4,551,023

[45] Date of Patent: Nov. 5, 1985

[54] SYSTEM FOR RECORDING INFORMATION ON PHOTOGRAPHIC IMAGE DENSITY AND PROCESS

[75] Inventor: Kenji Nakauchi, Kanagawa, Japan

[73] Assignee: Fuji Photo Film Co., Ltd., Kanagawa, Japan

[21] Appl. No.: 539,244

[22] Filed: Oct. 5, 1983

[30] Foreign Application Priority Data

Oct. 6, 1982 [JP] Japan ................................. 57-175942
Nov. 1, 1982 [JP] Japan ................................. 57-190783

[51] Int. Cl.$^4$ ............................................ G01N 21/00
[52] U.S. Cl. .................................... 356/444; 356/404
[58] Field of Search ....................... 356/404, 443, 444; 355/68

Primary Examiner—Bernard D. Pianalto
Attorney, Agent, or Firm—Sughrue, Mion, Zinn, Macpeak, and Seas

[57] ABSTRACT

The invention relates to a system for recording information on the densities of various points of a photographic image such as a negative film by means of a photoelectric converter. The information on densities that change by small degrees as the image is scanned from its periphery toward the center is eliminated, and, if desired, the information on the density for areas discrete from the area having the density corresponding to the eliminated information and which has a density substantially the same as the density of that area is also eliminated.

16 Claims, 15 Drawing Figures

SYSTEM FOR RECORDING INFORMATION ON PHOTOGRAPHIC IMAGE DENSITY AND PROCESS

BACKGROUND OF THE INVENTION

The present invention relates to a system for recording information on photographic image density, and more particularly, to a system which eliminates information on the density of unimportant areas of a photographic image, with the result that the possible noise that will interfere with the drawing of density information from the important area of the photographic image is reduced.

Photographic printing devices or other photographic devices are equipped with a recorder for photographic image density (hereunder simply referred to as density). This machine is capable of efficient recording of the density of each image frame (hereunder simply referred to as a frame) of an original film to be printed such as a negative or positive film (hereunder simply referred to as negative film or the like). The most important thing about this recorder is that it be capable of recording the same density information from the same scene on the negative film or the like irrespective of any change in the background. To meet this end, the conventional recorder draws the density information only from the center of the frame of the negative film or the like because it is empirically established that the principal part of the scene is highly probably positioned in the center of the frame. However, this practice causes a serious error if the principal part of the scene is not in the center of the frame.

SUMMARY OF THE INVENTION

The primary purpose of the present invention is to provide a system for recording density information that is free from the above described problem with the conventional system. According to the system of the present invention, density information from unimportant areas (other than the principal part) of the scene in the frame of a negative film or the like is eliminated so as to increase the weight of the density information from the principal part of the scene in the frame.

One aspect of the present invention relates to a system for recording the information on the densities at various points of a negative film or the like by means of a photoelectric converter, wherein the information on densities that change by small degrees as the image area is scanned from its periphery toward the center is eliminated. This elimination is based on our finding that the principal part of the scene is seldom positioned in the marginal portion of the frame.

According to another aspect of the present invention, not only is the information on the densities that change by small degrees as the image area is scanned from its periphery toward the center eliminated, but the information on the density for an area discrete from the area having the density corresponding to the eliminated information and which has a density substantially the same as the density of that area is eliminated as well.

The operating principle of the present invention is based on the finding that the principal part of the scene is rarely framed around the margin of a negative film or the like. Therefore, in a first step, the system of the present invention regards the periphery of the frame as the unimportant area of the scene. Then, the area which is the same in density (or both density and color) as that unimportant area is regarded as equivalent to that unimportant area.

The unimportant part of the scene may be determined by checking the image to see if it is continuous from the periphery toward the center in four directions, for example, from top to bottom, from bottom to top, from left to right and from right to left. The continuity of the image can be checked by several methods. In one method, the full frame is scanned once to obtain the difference between maximum density and minimum density, and two areas are regarded as being discontinuous if their densities differ from each other by a value greater than a given fraction (e.g. 1/10) of that difference. In another method, the density of the full frame is differentiated in four directions, and two areas are regarded as being discontinuous if the differential is greater than a given fraction (e.g. 1/10) of the difference between the maximum and minimum densities.

In order to avoid the possibility of erroneous elimination of the information on the principal part of the scene, the system of the present invention may be designed so that it will not eliminate the center of the frame unconditionally or such that it will not regard as continuous the areas that reach the center of the frame. These features are effective for taking a close-up shot of the background or a human model. In the case of a frame showing the sky beyond a window or one looking through foliage, the unimportant area (i.e. the sky) of the scene does not reach the periphery of the frame. Even in this case, the object of the present invention can be achieved by eliminating the area that is regarded as being equal in density and color to the relatively large area that is eliminated by the criterion of continuity from the periphery of the frame.

BRIEF DESCRIPTION OF THE DRAWINGS

The system of the present invention is hereunder described in detail by reference to the embodiments shown in the accompanying drawings, in which.

DETAILED DESCRIPTION OF THE PREFERRED EMBODIMENTS

Figure 1:
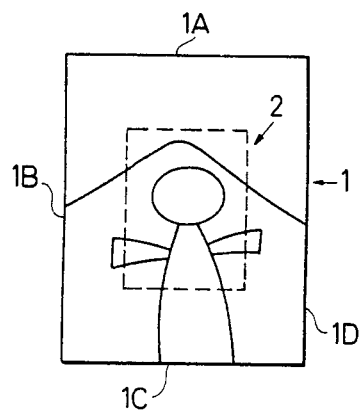
FIG. 1 shows an example of an image on a negative film.

FIG. 1 shows an image on a negative film according to one embodiment of the present invention. In FIG. 1, the frame of the negative film generally indicated at 1 includes a center area 2 determined on the basis of, say, the probability of the average principal part of the scene being framed within the negative film. The four sides of the frame are designated by 1A to 1D.

According to the embodiment illustrated by FIG. 1, the full frame of the negative film is scanned by a photoelectric converter, and the density information from each picture element (pix) is stored in a memory and subjected to processing in a CPU. More specifically the frame 1 is scanned in four directions, e.g., from top to bottom, from bottom to top, from right to left and from left to right, and the density information that is read from a specific pix is compared with the information from the immediately adjacent pix. If a substantial difference is recognized between the two pieces of density information, both are accepted, and if no difference is found, the information from the immediately adjacent pix is discarded. By repeating this procedure, correct density information can be recorded irrespective of any change in the background.

The procedure described above is adequate to ensure the practical recording of photographic image density, but in order to achieve greater accuracy, a second stage of processing may be added after a certain set of specific density information has been discarded in the first stage as described above. In the second stage of processing, the density information obtained from areas which have the same density value as that of the eliminated information, and which are composed of pixes discrete from those corresponding to the discarded information, is discarded. By repeating the first and second stages of processing, correct density information can be more accurately obtained irrespective of any change in the background.

Figure 2:
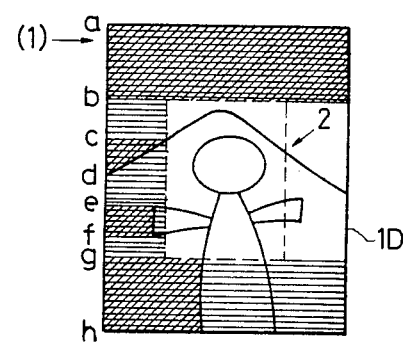
FIGS. 2 to 5 show the density information discarded as a result of a first stage of processing by scanning the image in four directions, from left to light, from bottom to top, from right to left and from top to bottom, according to one embodiment of the present invention.

The processing method according to the present invention will be hereunder described in greater detail. FIG. 2 shows, on the frame 1, the density information to be discarded as a result of the first stage of processing, on the basis of readings from the memory in response to the scanning of the frame from the left-hand side as indicated by the arrow (1). In the area (a-b), the readings taken continue to the right side 1D of the frame without any change in density, and thus all the information for this area is discarded, as indicated by the crosshatched lines. In the area (b-c), the readings continue to the center area 2 without any change in density, but the information for this area is not discarded because the continuity of the absence of density change reaches into the center area 2. In the area (c-d), a change in density occurs before the readings reach the center area, so the information corresponding to the pixes scanned before the detection of that change (these pixes are on the left-hand side of the center area in FIG. 2) is discarded. The readings are analyzed and processed as above, continuing to the bottom of the frame 1. As a result, the data for the crosshatched area of FIG. 2 is discarded.

Figure 3:
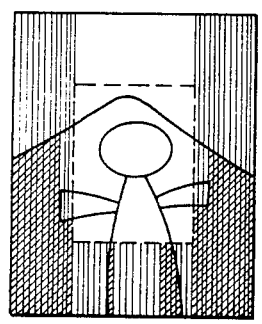
Figure 4:
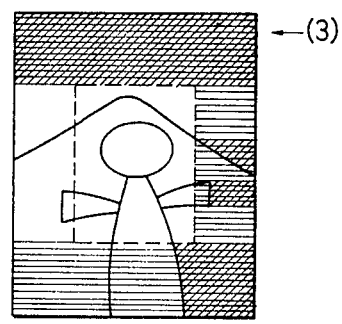
Figure 5:
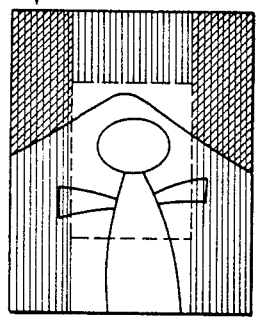

The same procedure is how repeated, but in the other three directions, viz. from bottom to top, from right to left and from top to bottom as shown in FIGS. 3 to 5. The areas containing density information which is discarded are crosshatched in the respective Figures, and the discarded areas are combined into the hatched area in FIG. 6. As is clear from FIG. 6, the first stage of processing according to the system of the present invention is sufficient to eliminate the greater part of the background information not necessary for determining the amount of exposure of a printing device or other photographic devices.

Figure 6:
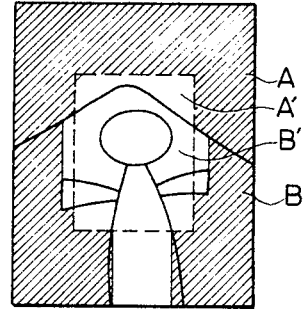
FIG. 6 is a combination of FIGS. 2 to 5.
Figure 7:
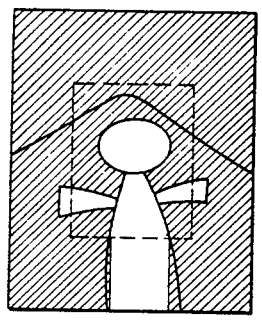
FIG. 7 shows the result obtained by subjecting the frame of FIG. 6 to a second stage of processing.

The frame shown in FIG. 6 is then subjected to the second stage of processing. The values of the individual pieces of density information discarded in the first stage of processing are aggregated, and if the aggregate is found to be greater than a predetermined value representing the combination of the density information for the sky (area A) and the mountain (area B) in the background, the areas which provide substantially the same density information and which have not been discarded in the first stage of processing, that is, the sky (A') in the center area and the mountain (B') both within and outside the center area, are determined. In the second stage of processing, the density information for these areas is additionally discarded, and the result is shown in FIG. 7. By combining the first and second processing stages, only the density information for the background, which is truly unnecessary for determining the amount of exposure for the printing device or other photographic devices is eliminated. Therefore, the determination of a precise exposure can be accomplished using the system of the present invention.

Figure 8:
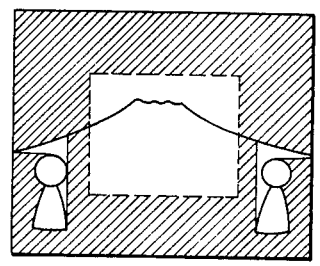
FIGS. 8 to 13 show other embodiments of the present invention.

Non-professional photographers like taking outdoor pictures of a human model standing against a background such as the sky or a mountain. FIG. 8 shows an example of this kind of photo after being subjected to the first stage of processing according to the present invention. Obviously, the density information for the center area and that for the two standing human models is recovered with a very high selectivity while the unwanted information is eliminated very precisely. It is therefore possible to determine the correct amount of exposure on the basis of the recovered information. As in the case of the frame of FIG. 7, the frame of FIG. 8 may also be subjected to the second stage of processing in order to discard the density information obtained from the sky and mountain in the background. A frame of the type shown in FIG. 8 would produce a serious error in density information if processed by the conventional system of recovering only the information from the center of the frame, but even such a frame can be accurately processed by the system of the present invention.

Figure 9:
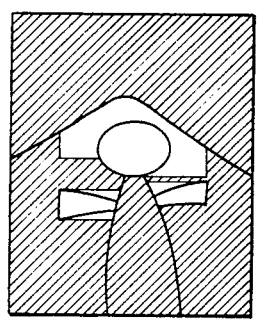
Figure 10:
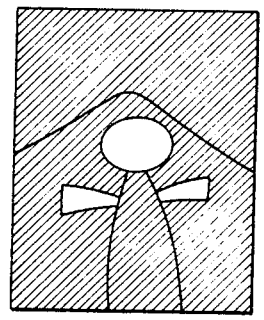

Another embodiment of the present invention is illustrated in conjunction with FIG. 9, which embodiment differs from the first embodiment in that it does not use the center area 2. As in the first embodiment, the frame 1 of a negative film is scanned from the periphery toward the center in four directions and the density information for individual pixes is read from the memory, and the information for one pix is compared with the information on the immediately adjacent pix. If the difference is less than a predetermined value, the latter is discarded. By this first stage of processing, only the density information for the unhatched area in FIG. 9 is recovered. Subsequently, the frame is subjected to the second stage of processing on the basis of the results obtained in the first stage of processing. As shown in FIG. 10, only the density information for the unhatched area is recovered after performing the second stage of processing. The greatest advantage of the second embodiment described above is that it can be implemented with simpler logic than the case of the first embodiment using the center area.

Figure 11:
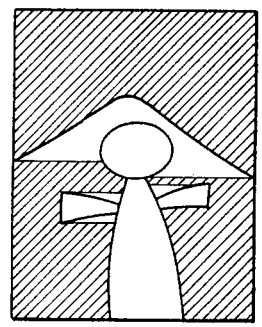

A variation of the second embodiment is shown in FIG. 11, wherein the unhatched area indicates the density information recovered by scanning the frame in three directions but not in the upward direction. The advantage of this variation is that it ensures more exact processing of a negative film including the upper half of a human body as the principal part of the scene.

Figure 12:
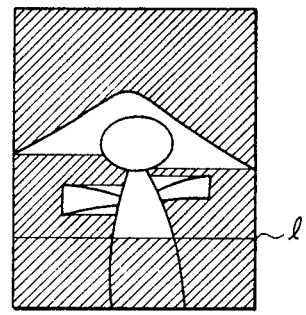

Another variation of the second embodiment is shown in FIG. 12, wherein the unhatched area indicates the density information recovered by scanning the frame in four directions, but effecting the reading of density information in response to upward scanning to a point not farther than a predetermined level (indicated by the line 1 in FIG. 12). In this variation, a negative film including the upper half of a human body as the principal part of the scene can be processed more precisely than with the variation shown in FIG. 11.

Figure 13:
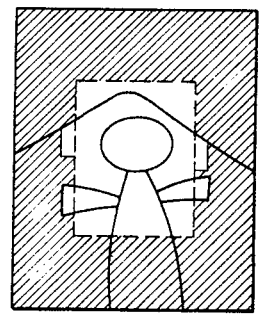

FIG. 13 shows a third embodiment of the present invention wherein the frame of a negative film other than the central area thereof is processed as in the embodiment of FIG. 9. According to this embodiment, the central area is left intact, whereby the risk of eliminating the density information for the principal part of the scene is reduced.

If the density information to be eliminated by the system of the present invention indicates the color of human skin, the system may be designed so that such information is not eliminated. By incorporating this special design feature, even a frame wherein a human model or other principal part of the scene is positioned very close to the marginal portion can be correctly processed. The color of human skin can be detected by the technique disclosed in Japanese Patent Application Laid Open No. 156624/77.

In the three embodiments described above, density information is read from the memory in response to the results of scanning in four directions, from left to right, from bottom to top, from right to left and from top to bottom, in the stated order. But it should be understood that the scanning order and direction may be freely determined.

The density information recorded by the system of the present invention may be directly used in exposure control for a printing apparatus, or, alternatively, it may be optionally combined with other photographic parameters to determine the appropriateness of a pattern on negative films.

In the system of recording photographic image density according to the present invention, the density information for specific pixes can be read by a known technique, for example, by the apparatus shown in Japanese Patent Application Laid Open No. 153334/81 (corresponding to Japanese Patent Application No. 57262/80 and U.S. patent application Ser. No. 258,699).

A specific embodiment of the present invention, which is applied to an exposure determining device for a printing device, is hereunder described.

Figure 14:
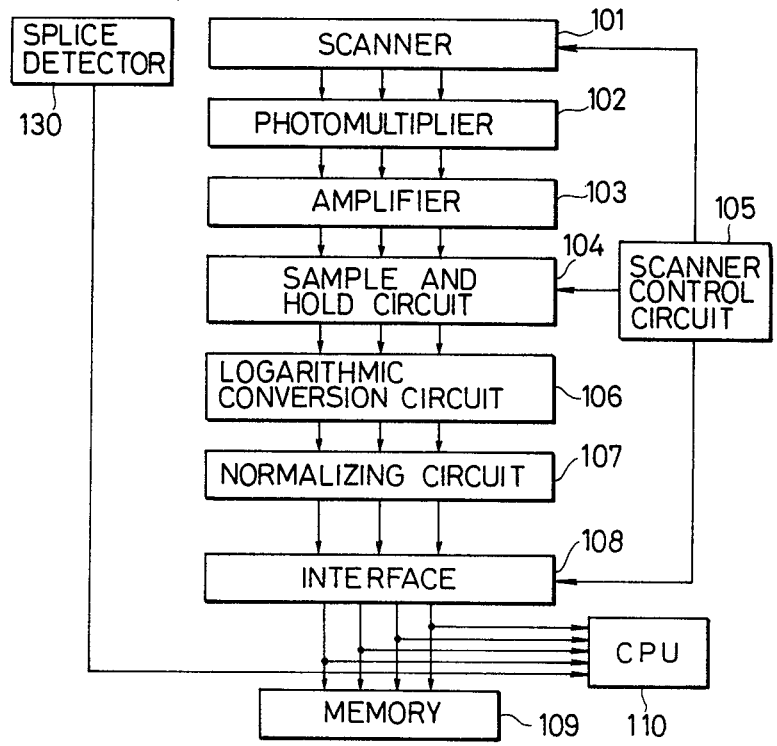
FIG. 14 is a block diagram of an exposure determining device that may be used to implement the system of the present invention.

FIG. 14 is a block diagram showing the essential parts of the exposure determining device. The surface of a color picture film is scanned by a scanner 101 and a light beam transmitted through or reflected from the film is separated into three light beams (blue, green and red light beams) by a color separating optical device. The three color light beams are applied to a photomultiplier 102 having blue, green and red light receiving elements, where they are separately measured.

The output measurement signals of the photomultiplier 102, after being amplified individually by an amplifier 103, are applied to a sample-and-hold circuit 104 where they are sampled and held. The sample-and-hold circuit 104 is controlled by a sampling pulse output by a scanner control circuit 105. As the scanning section of the scanner 101 is controlled by the scanner control circuit 105, the sample-and-hold process is carried out in synchronization with the scanner 101, thus providing a number of measurement points which are regularly arranged on the surface of the color film. For instance in the case of a 35-mm color film having an area $22 \times 34$ mm$^2$, (omitting the periphery), each frame is scanned at intervals of 1 mm with solid points 1 mm in diameter, which points will be enlarged to points about 3 mm in diameter on the color print. Accordingly, the picture surface is measured using 748 ($=22 \times 34$) measurement positions. The blue, green and red measurement signals of each measurement point sampled by the sample-and-hold circuit 104 are applied to a logarithmic conversion circuit 106 where they are subjected to logarithmic conversion to calculate the blue density B, green density G and red density R. More specifically, if the transmissivity is represented by T, (log 1/T) is calculated using circuit 106.

The blue, green and red densities B, G and R are applied to a normalizing circuit 107 where they are subjected to γ-correction and sensitivity correction according to the photosensitive material employed. Different γ-values and sensitivity values representing the relations between exposure data and density are provided by different film manufacturers for different types of films. Accordingly, even if the same object is photographed under the same conditions, different types of films will have different densities.

Accordingly, γ-correction is carried out as follows: A key is provided for every type of film to be processed. The keys are selectively operated according to the type of film and the density signals are corrected by adding predetermined constants thereto using an adder. Thereafter, the gain of the amplifier is adjusted so that the density signals thus corrected are multiplied by a correction factor. In this manner, γ-correction is achieved.

By this method, the density signals are modified so that the same densities are provided for the same object. The blue, green and red densities B, G and R of the measurement point are supplied to an interface B and are stored in a memory 109 at corresponding addresses specified by measurement position signals outputted by the scanner control circuit 105. After the entire area of the negative film has been scanned, the data is read out of the memory 109 to a CPU (central processing unit) 110. In the CPU, processing is carried out and then the desired amount of exposure is calculated in order to control the exposure for printing.

In the case where the device is off-line with respect to the color printer, the exposure data is recorded on punched tape or magnetic tape to later control the color printer.

Figure 15:
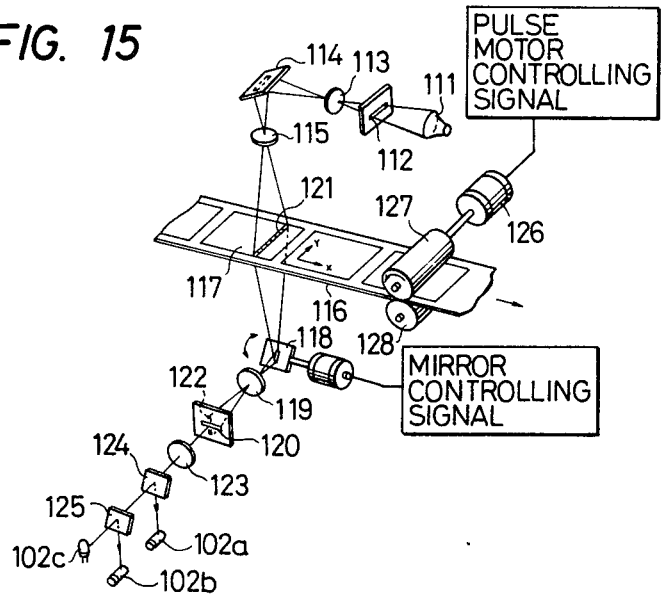
FIG. 15 is a perspective view showing the essential parts of the scanner of the device of FIG. 14.

FIG. 15 is a perspective view showing essential components of the scanner for measuring the transmission density of a negative film. An illuminating light beam emitted from a light source 111 passes through an elongated slit 112 and a lens 113 and falls on a reflecting mirror 114, as a result of which the illuminating light beam is bent downwardly by the reflecting mirror. Then, the illuminating light beam passes through a lens 115 to the picture surface 117 of a color film 116 to illuminate the picture surface widthwise. That is, a belt-shaped light beam is applied to the picture surface.

The belt-shaped light beam passed through the color picture film 116 is reflected by a scanner mirror 118 disposed below the film. The light beam thus reflected passes through a lens 119 prior to reaching a slit 120. The scanner mirror 118 may be fabricated by mounting a mirror on a galvanometer. The scanner mirror is swung by a sawtooth wave signal, i.e. a mirror control signal, output by the scanner control circuit 105 in FIG. 14.

The image 122 of a belt-shaped part 121 of the picture surface 117 of the illuminated color film is formed on the slit 120 in a manner such that the image 122 is perpendicular to the slit 120. As the scanner mirror 118 is swung at a predetermined speed in response to the mirror control signal, the image 122 is moved perpendicularly to the slit 120. Accordingly, different parts of the image 122 pass through the slit 120 as the image moves from one end to the other.

The light beam, after it has passed through the slit 120, is applied through a lens 123 to dichroic mirrors 124, 124 where it is separated into three color beams, red, blue and green. The three color beams are applied to photomultipliers 102a, 102b and 102c where the quantities of light thereof are separately measured.

The picture surface 117 is scanned in the Y-direction by the scanner mirror 118, then moved in the X-direction by a predetermined pitch, then scanned again in the Y-direction by the scanner mirror 118. To accomplish this, when the scanner mirror 118 returns to the original position after completing a scanning operation, the scanner control circuit 105 outputs a pulse motor control signal to rotate a pulse motor 126 through a predetermined angle.

A film feeding roller 127 is coupled to the pulse motor 126 and the color film 116 is held between the film feeding roller 127 and a roller 128 so that the film 116 is moved by a predetermined distance, for example 1 mm. Thus, the density data of each part of the picture surface 117 of the color picture film 116 is measured.

The measured density information is stored in memory 109 at designated addresses, and from that memory, the data for each reading direction is read into CPU 110, which calculates the desired exposure on the basis of the density information left after removing information on densities that change by small degrees as the photographic image area is scanned from its periphery toward the center. The calculated exposure is sent as a control signal to determine the proper amount of exposure for the printer.

As described in the foregoing, the present invention provides a system of recording the information on the densities at various points of a negative film or the like by means of a photoelectric converter, wherein density information that changes by small degrees as the image area is scanned from its periphery toward the center is eliminated. If necessary, the density information for an area that is discrete from the area having a density corresponding to the eliminated information and which has a density substantially equal to the density of that area is also eliminated. By so doing, only the density information for the area other than the principal part of the scene in the frame of the negative film or the like is selectively eliminated, with the advantageous result of increasing the weight of the density information from the principal part of the scene.

What is claimed is:

1. In a system for recording information on the densities of various points of a photographic image such as a negative film by means of photoelectric conversion, the improvement comprising means for eliminating that information on densities which change by small degrees as the image area is scanned from its periphery toward the center.

2. In a system for recording information on the densities of various points of a photographic image such as a negative film by means of photoelectric conversion, the improvement comprising means for eliminating first information on densities which change by small degrees as the image is scanned from its periphery toward the center, and for further eliminating the information on the density of areas discrete from the area having the density corresponding to said first eliminated information, and which has a density substantially the same as the density of said area.

3. A system as claimed in claim 1, including means for scanning said image, means for storing density information on discrete locations of said image, and means for reading said stored density information in a plurality of reading directions with respect to said image.

4. A system as claimed in claim 3, wherein said reading means reads said density information, with respect to said image, from left to right, bottom to top, right to left and top to bottom.

5. A system as claimed in claim 4, wherein said reading means comprises means for eliminating the density information which changes by small degrees from the reading starting direction toward the opposite direction and for retaining that information following a density discontinuity.

6. A system as claimed in claim 5, further including means for defining a central portion of said image, said reading means retaining that density information which changes by small degrees from the reading starting direction toward the opposite direction and which reaches into said central portion.

7. A system as claimed in claim 3, wherein said reading means reads said density information, with respect to said image, from left to right, right to left and top to bottom.

8. A system as claimed in claim 7, wherein said reading means comprises means for eliminating the density information which changes by small degrees from the reading starting direction toward the opposite direction and for retaining that information following a density discontinuity.

9. A system as claimed in claim 3, wherein said bottom to top reading is performed by said reading means only to a predetermined line defined with respect to said image.

10. A system as claimed in claim 5, said reading means further retaining density information corresponding to a human skin tone.

11. A system as claimed in claim 2, including means for scanning said image, means for storing density information on discrete locations of said image, and means for reading said stored density information in a plurality of reading directions with respect to said image.

12. A system as claimed in claim 11, wherein said reading means reads said density information, with respect to said image, from left to right, bottom to top, right to left and top to bottom.

13. A system as claimed in claim 12, wherein said reading means comprises means for eliminating the density information which changes by small degrees from the reading starting direction toward the opposite direction and for retaining that information following a density discontinuity.

14. A system as claimed in claim 13, further including means for defining a central portion of said image, said reading means eliminating density information from said central portion only when said information is continuous with priorly eliminated density information outside of said central portion.

15. A method of exposure control for a photographic apparatus, comprising;

(a) scanning a photographic image to obtain density information with respect to a plurality of discrete locations of said image,
(b) reading said density information with respect to at least three directions relative to said image,
(c) eliminating that density information which exhibits only a small degree of change as the density information is read from the periphery of said image toward the center thereof, while retaining density information corresponding to areas following a density discontinuity, and
(d) determining an exposure value using the remaining retained density information.

16. A method as claimed in claim 15, wherein, following said first elimination of density information, further eliminating density information respecting areas discrete from areas having the density corresponding to said first eliminated information and which have densities substantially the same as the density of said first eliminated information.

* * * * *